April 4, 1961 M. E. WYANT Plant Pat. 2,042
ROSE PLANT
Filed June 11. 1958
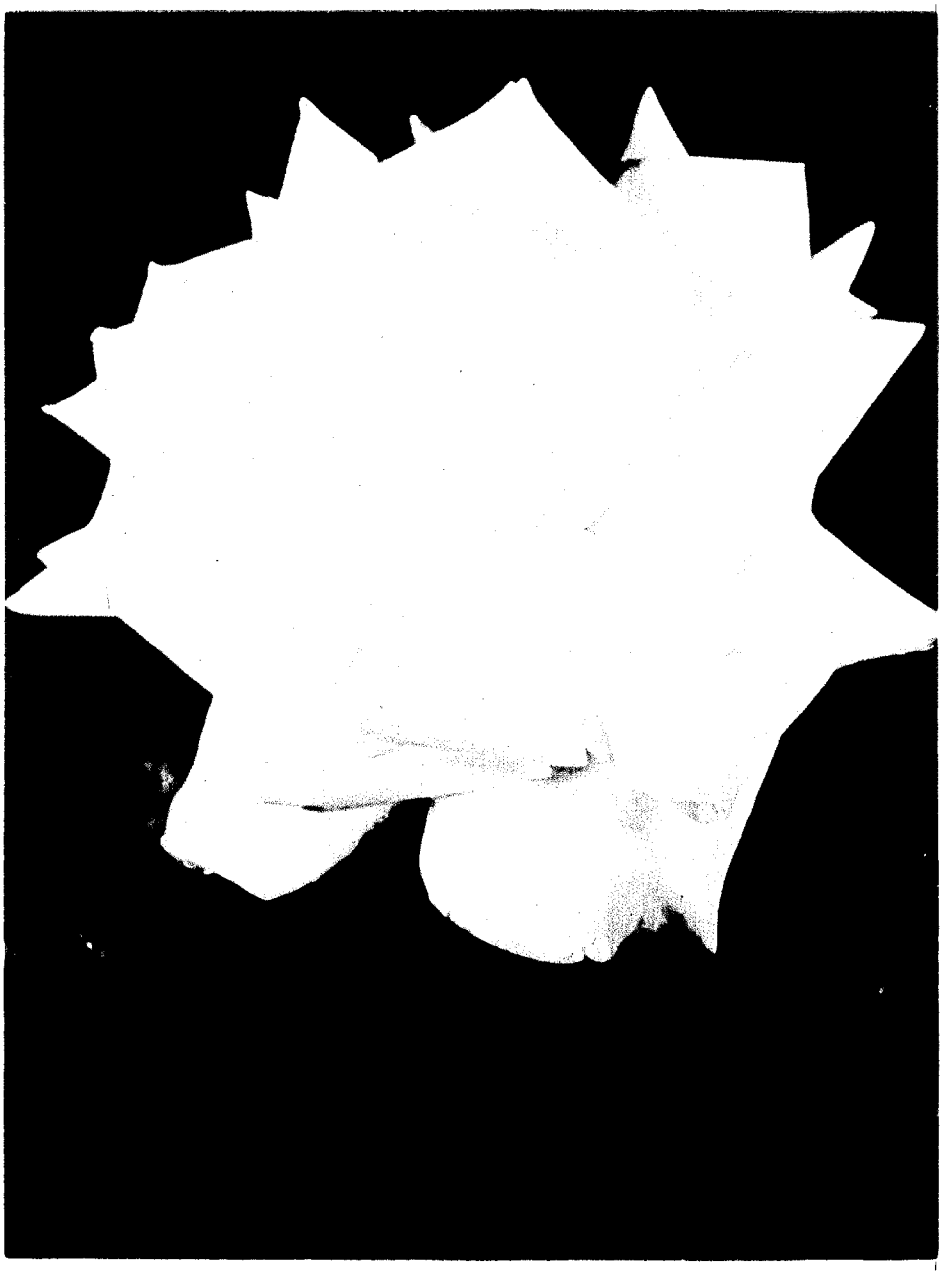
Inventor:
M. E. Wyant
by
Robb & Robb
attorneys United States Patent Office Plant Pat. 2,042
Patented Apr. 4, 1961

2,042

ROSE PLANT

Melvin E. Wyant, Johnny Cake Ridge, Mentor, Ohio

Filed June 11, 1958, Ser. No. 741,436

1 Claim. (Cl. 47—61)

My present invention comprises a new and distinct variety of rose plant, the result of crossing the variety "Mrs. Charles Lamplough" (unpatented) and the variety "Peace" (Plant Patent No. 591).

The primary object of my invention was to produce a new variety of rose plant having larger and better formed flowers than those of previously known similar varieties. This objective was fully attained, and as a result thereof, my new variety is particularly characterized by its larger, more double, many petalled, better formed flowers, and its healthy, vigorous and free blooming habit of growth.

The flowers of my new variety take their whiter color from the parent variety "Mrs. Charles Lamplough" and the flowers of my new variety have a yellowish tinge derived from the parent variety "Peace." However, the flowers of my new variety are whiter and more high centered than those of "Peace," and the flowers of my new variety have more petals which re-curl better.

As compared with "Mrs. Charles Lamplough," my new variety has flowers which are more double and higher centered with many more petals which are more re-curling.

My new variety is a much sturdier grower than "Mrs. Charles Lamplough" being endowed with strong and vigorous habits of growth and sturdiness similar to those of "Peace."

My new variety has been found to retain its distinctive characteristics through successive asexual reproduction. Asexual reproduction has been accomplished by budding at Mentor, Ohio.

The accompanying drawing forming a part hereof shows a typical specimen of the flower of my new variety.

The following is a detailed description of my new variety of rose plant, the color references being to the Nickerson Color Fan, published by Munsell Color Company:

Parentage: Seedling.
*Seed parent.*—"Mrs. Charles Lamplough."
*Pollen parent.*—"Peace."
Classification: Hybrid tea.

*Flower*

(Observations made from a plant that was grown in a greenhouse early in December at Mentor, Ohio, U.S.A.)

Blooming habit: Intermittent.
Bud:
*Size.*—Very large.
*Form.*—Ovoid; wet weather tends to make it ball; not affected by hot weather.
*Color.*—When sepals first divide—very pale yellowish green, Plate 9, blotched with light red, Plate 1. When petals begin to unfurl—very pale greenish-yellow, Plate 8. When half blown: inside of petals—very pale yellow with light yellow, Plate 7, at base; reverse of petals—same coloring.
*Sepals.*—Smooth edge.
*Calyx.*—Shape—funnel. Size—small. Aspect—smooth. Odor when rubbed—none.
*Peduncle.*—Long. Aspect — smooth. Color — Bronzy. Strength—stiff. Opening—bud does not always open well and is affected by adverse weather conditions.

Bloom:
*Size.*—Very large. Average size when fully expanded—5½ inches.
*Borne.*—Singly.
*Stems.*—Medium length; normal strength.
*Form.*—When first opened—high centered. Permanence—like a show dahlia.
*Petalage.*—Very double. Number of petals under normal conditions—70 to 100.
*Color.*—Center of flower—Munsell hue 2.5Y–8/12 vivid yellow to white. Outer petals—lighter than Munsell hue 5Y–9/9 brilliant yellow, blotched with Munsell hue 2.5R–7/8 strong pink. Base of petals (singlet)—lighter than Munsell hue 5Y–9/9 brilliant yellow. Inside of petals—lighter than Munsell hue 5Y–9/9 brilliant yellow to white toward tips. Reverse of petals—much lighter than Munsell hue 5Y–9/9 brilliant yellow to white toward tips. General tonality from a distance—much lighter than Munsell hue 5Y–9/9 brilliant yellow.
*Discoloration.*—General tonality at end of first day—lighter than Munsell hue 5Y–9/9 brilliant yellow. Second day—lighter than Munsell hue 5Y–9/9 brilliant yellow. Third day—lighter than Munsell hue 7.5Y–9/8 brilliant greenish yellow.

Petals:
*Texture.*—Soft; not affected by wet or hot weather.
*Appearance.*—Inside—satiny. Outside—satiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Large; few.
*Color.*—Munsell hue 7.5R–3/8 moderate reddish brown.
*Arrangement.*—Regular round styles.
Stamens, filaments (threads): short. Color—Munsell hue 7.5Y–9/8 brilliant greenish yellow.
Pollen: Munsell hue 7.5Y–9/8 brilliant greenish yellow.
Styles: Loosely separated; uneven; short; thin.
Stigmas: Color—Munsell hue 2.5P–9/1 purplish white.
Ovaries: All enclosed in calyx.

*Plant*

Form: Bush.
Growth: Vigorous.
Foliage: 5 leaflets.
*Size.*—Medium.
*Quantity.*—Normal.
*Color.*—New foliage: upper side—Munsell hue 10GY–5/8 strong yellowish green; under side—Munsell hue 10GY–4/6 dark yellowish green. Old foliage: upper side—Munsell hue 2.5G–4/6 dark yellowish green; under side—Munsell hue 2.5G–5/9 strong yellowish green.

*Shape.*—Oval.

*Texture.* — Upper side — smooth. Under side — smooth.

*Ribs and veins.*—Ordinary.

*Edge.*—Serrated (saw-toothed).

*Serration.*—Small.

*Leaf stem.*—Color—green. Under side—smooth.

*Stipules.*—Medium; smooth.

*Disease resistance.*—Resistant to black spot and mildew, as observed in plants grown in gardens at Mentor, Ohio, and elsewhere throughout the United States.

Wood:

*New wood.*—Color—Munsell hue 5GY–7/0 strong yellow green. Bark—smooth.

*Old wood.*—Color—Munsell hue 5GY–6/8 to 5/6. Bark—smooth.

Thorns:

*Thorns.* — Quantity — on main stalk — ordinary. Form—narrow base. Color (when young)—

Munsell hue 5R–3/7, dark red. Position—irregular.

*Prickles.*—Quantity: on main stalk—ordinary; on laterals—none.

*Short needles.*—Quantity: on main stalk—few; on laterals—few.

I claim:

A new and distinct variety of rose plant of the hybrid tea class, substantially as shown and described, characterized by its larger, more double, many petaled, better formed flowers, and its healthy, vigorous, and free blooming habit of growth.

References Cited in the file of this patent

UNITED STATES PATENTS

| | | |
|---|---|---|
| P.P. 1,688 | Boerner | Mar. 11, 1958 |
| P.P. 1,762 | Boerner | Oct. 14, 1958 |
| P.P. 1,770 | Shepherd | Nov. 11, 1958 |